United States Patent [19]

Szantay et al.

[11] 4,243,660
[45] Jan. 6, 1981

[54] COMPOSITE INSECT ATTRACTANT FOR MALE CABBAGE MOTHS AND A PROCESS FOR PREPARING ITS ACTIVE AGENTS

[75] Inventors: Csaba Szantay; Lajos Novák; Miklos Toth; Jozsef Balla; Bela Stefko, all of Budapest; Attila Kis-Tamas, Pilisvörösvár, all of Hungary

[73] Assignee: Egyt Gyógyszervegyészeti Gyár, Budapest, Hungary

[21] Appl. No.: 31,583

[22] Filed: Apr. 19, 1979

[30] Foreign Application Priority Data

Apr. 21, 1978 [HU] Hungary ............... EE 2558

[51] Int. Cl.³ .................. A01N 25/00; A01N 37/06
[52] U.S. Cl. ................... 424/84; 424/314; 560/255; 560/261; 560/262
[58] Field of Search .............. 424/84, 314; 560/261

[56] References Cited

U.S. PATENT DOCUMENTS

| 4,042,681 | 8/1977 | Underhill et al. | 424/84 |
| 4,059,689 | 11/1977 | Struble et al. | 424/84 |
| 4,107,293 | 8/1978 | Swailes et al. | 424/84 |

OTHER PUBLICATIONS

Beroza, "Pest Management with Insect Sex Attractants", A.C.S. Symposium Series 23, A.C.S., Wash. D. C. (1976), Compd. 96.

Primary Examiner—Allen J. Robinson
Attorney, Agent, or Firm—Karl F. Ross

[57] ABSTRACT

The invention relates to a composite insect attractant for male cabbage moths (*Mamestra brassicae*) containing (Z)-11-hexadecenyl acetate and (Z)-11-heptadecenyl acetate as active agents in a weight ratio of 70 to 90:80 to 1, optionally along with a liquid or solid adjuvant. An insect trap can contain the composition which is used for attracting and trapping cabbage moth. Their mating is disrupted by air permeation techniques. (Z)-11-heptadecenyl acetate is a synergistically active new compound. The composition according to the invention produces a significantly stronger stimulating reaction on male cabbage moths than the known sex lure compositions.

5 Claims, No Drawings

COMPOSITE INSECT ATTRACTANT FOR MALE CABBAGE MOTHS AND A PROCESS FOR PREPARING ITS ACTIVE AGENTS

FIELD OF THE INVENTION

The invention relates to a composite insect attractant for male cabbage moths. More particularly, the invention relates to a composition containing a synergistic combination of two active agents. Another object of the invention is to provide an improved insect trap. A still further object of the invention is to provide an improved process for attracting and trapping cabbage moths as well as for disrupting their mating. The invention relates further to (Z)-11-heptadecenyl acetate, a new compound synergistically combinable with earlier attractants as well as to a novel process for the preparation of this new compound and the known (Z)-11-hexadecenyl acetate, which are the active ingredients of the composition according to the invention.

BACKGROUND OF THE INVENTION

As known, the cabbage moth is a wide-spread pest, causing recurring damage in vegetables annually, primarily to cabbages and cauliflowers. Phosphoric acid esters were hitherto used to combat this pest; these compounds, however, do not exert a selective effect and are highly toxic to humans.

The problems of environmental pollution emerging in connection with the use of conventional pesticide chemicals can be eliminated for the Lepidoptera group when compositions containing the natural sex lures (sex pheromones) of the species to be combatted are used as insecticides. Sex pheromones are excreted by the females, and the males of the species can find the females to mate with them by the aid of the characteristic scent of the pheromone.

Pheromones can be used in plant protection in two ways. According to the first method, traps are baited with the sex pheromone and seize the male moths attracted by the active agents. In this way information can be obtained on the appearance of the pest, i.e. the prospective damage can be forecast. This method has the advantage over other forecasting methods utilizing traps that the pheromone-containing traps recover only the preselected pest, whereas light or UV devices trap practically all kinds of insects flying by night. Moreover, the pheromone-containing traps indicate the beginning of swarming generally more sensitively than do light traps [Mani et al: Schweiz. Z. Obst. Weinbau 81, 337-344 (1972)]. When the direct environment of the traps is treated with an insecticide, the majority of the male population attracted perishes in this killing zone, so that the risk of environmental pollution is restricted only to the killing zones, i.e. decreases to a considerable extent.

According to the second method, the so-called method of air permeation, the ability of males and females to find each other is distorted, thus their mating can be disrupted. In this instance a relatively greater amount of pheromone is emitted into the air over the plant culture to be protected, whereupon the males sense the presence of the pheromone everywhere. Thus they get confused and become unable to find the females. When pheromones are utilized according to this method, they are to be applied in far lower dosages than the classicial insecticides [W. L. Roefols and R. T. Cardé: Ann. Rev. Entomol. 22, 377-405 (1977)].

The prior trapping technologies applied to protect plants against cabbage moths have the disadvantage that they cannot indicate the initial damage in due time; thus a protective treatment can be performed generally only when the elder caterpillars have already reached the internal parts of the plants and have become practically unavailable for the classical insecticides (e.g. phosphoric acid esters). When the sex pheromone of cabbage moths is applied in the trapping technique, this disadvantage can be eliminated.

Pheromones can also be used to advantage in the air-permeation technique since they are extremely selective and are nontoxic to vertebrates.

Szentesi et al [Act. Phytopath. Acad. Sci. Hung. 10, 425-429 (1975)] report on the extraction of the pheromone of cabbage moth, but they do not disclose the structure of the pheromone. Having isolated and analyzed this pheromone, Bestmann et al [Tetrahedron Letters 6, 605-608 (1978)] established that the multicomponent pheromone system of the cabbage moth contains (Z)-11-hexadecen yl acetate as the major component, they were not able to identify, however, possible minor components of the complex pheromone.

H. I. Bestmann et al [Chem. Ber. 111, 248-253 (1978)] also report on the synthesis of several 1-substituted-(Z)-11-alkenes, among others, (Z)-11-hexadecenyl acetate and (Z)-11-octadecenyl acetate.

DESCRIPTION OF THE INVENTION

Now it has been found that when (Z)-11-hexadecenyl acetate, the known sex lure of cabbage moths, is combined with (Z)-11-heptadecenyl acetate, a novel compound synthesized by us for the first time, and when the resulting composition contains a major portion of (Z)-11-hexadecenyl acetate and a minor portion (about 1 to 30% by weight) of (Z)-11-heptadecenyl acetate, the composition has a synergistically enhanced effect and, even when emitted in a far lower concentration (e.g. than earlier attractants) into the air, produces a significantly stronger stimulating reaction on male cabbage moths than the known sex lure alone.

This observation is very surprising since, although two-component sex pheromones for other moth species have already been described (see, e.g. U.S. Pat. Nos. 4,042,681 and 4,059,689), these contain components differing from each other in two carbon atoms, whereas the two-component mixture according to the invention contains (Z)-11-hexadecenyl acetate of 16 carbon atoms in the alkenyl moiety in admixture with its direct homolog, (Z)-11-heptadecenyl acetate of 17 carbon atoms in the alkenyl moiety.

Thus, in one aspect, the invention relates to a novel composite insect attractant for male cabbage moths (*Mamestra brassicae*). This composition contains:

(a) (Z)-11-hexadecenyl acetate as active agent A and (b) (Z)-11-heptadecenyl acetate as active agent B in a weight ratio of (70 to 99 parts or percent of A):(30 to 1 part or percent of B), optionally along with a liquid and/or adjuvant.

The new compositions according to the invention contain components A and B preferably in a weight ratio of (85 to 95):(15 to 5). Of the liquid adjuvants, inert oily diluents are particularly preferred.

Furthermore, the invention relates to an insect trap for trapping male cabbage moths (*Mamestra brassicae*). This insect trap contains as active agent a combination of (Z)-11-hexadecenyl acetate (component A) and (Z)-11-heptadecenyl acetate (component B) in a total amount of 0.01 to 10.0 mg, preferably 1 to 3 mg, wherein the combination contains the two components in a weight ratio of (70 to 99 A):(30 to 1 B), optionally dissolved in a less volatile inert oil and/or formulated as a capsule.

In another aspect, the invention relates to a process for attracting and trapping male cabbage moths (*Mamestra brassicae*). According to this process, the males are exposed to the effect of an insect trap containing a combination of (Z)-11-hexadecenyl acetate (component A) and (Z)-11-heptadecenyl-acetate (component B) in a total amount of 0.01 to 10.0 mg, preferably 1 to 3 mg, wherein the combination contains the two components in a weight ratio of (70 to 99 A):(30 to 1 B).

In a still further aspect, the invention relates to a process for disrupting the mating of cabbage moths (*Mamestra brassicae*). According to this process, a combination of (Z)-11-hexadecenyl acetate (component A) and (Z)-11-heptadecenyl acetate (component B), containing the two components in a weight ratio of (70 to 99 A):(30 to 1 B) is emitted into the atmosphere. The above combination is emitted into the atmosphere generally with a speed of 1.0 to 20.0 mg/hectare/hr, preferably 3 to 10 mg/hectare/hr.

The invention relates further to the use of a preparation containing 70 to 99% by weight of (Z)-11-hexadecenyl acetate and 30 to 1% by weight of (Z)-11-heptadecenyl acetate as an insect attractant for male cabbage moths (*Mamestra brassicae*).

The invention also relates to (Z)-11-heptadecenyl acetate, a new compound which can be used in the above compositions and processes.

In a still further aspect, the invention rleates to a new method for the preparation of (Z)-11-heptadecenyl acetate, the novel compound according to the invention, as well as (Z)-11-hexadecenyl acetate, a compound synthesized by H. I. Bestmann et al.

The intermediates of the processes disclosed below are also considered part of our invention.

(Z)-11-Hexadecenyl acetate has been prepared, so far, by reacting an acetylene derivative with an appropriate halo compound [T. Ando et al: Agric. Biol. Chem. 41 (8) 1485] or via Wittig-condensation of the appropriate hydroxyaldehydes [H. I. Bestmann et al: Chem. Ber. 111, 248 (1978)]. Both methods require expensive starting substances and reactants, and run through difficult reaction steps (e.g. reaction with lithium aluminum hydride, ozonolytic decomposition, use of sodium hexamethyl disilazane, bicyclic boranes or lithium acetylide/ethylene-diamine complex, salt formation with acetylene and lithium amide and selective reduction in the presence of palladium-on-calcium carbonate).

According to the novel process of the invention, the compounds of the formula (I):

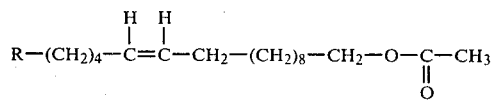

wherein R is hydrogen or methyl, are prepared as follows:

A known compound of the formula (VII):

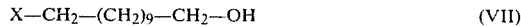

wherein X is halogen, is protected on the hydroxy group by a Y protecting group. As protecting group preferably tetrahydropyranyl, 1-ethoxyethyl or an acyl group is applied.

The protecting group is introduced into the formula (VII) compound preferably by reacting it with an excessive amount of 3,4-dihydro-2H-pyran, ethyl-vinyl-ether or an acylating agent, such as an acid anhydrode or an acyl halide. The reaction is performed preferably at room temperature, in the presence of an acid, preferably hydrochloric acid.

When the reaction is over, the excess of the reactant is removed from the mixture and the resulting compound of the formula (VI):

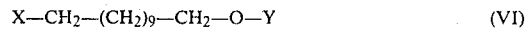

wherein X has the same meaning as defined above and Y stands for a protecting group, preferably tetrahydropyranyloxy, 1-ethoxyethyl or an acyl, particularly, acetyl, group, is reacted with triphenyl phosphine in a solvent medium, such as acetonitrile, in the presence of a base, e.g. potassium carbonate.

The reaction is performed preferably at elevated temperatures, such as at the reflux temperature of the mixture, for several hours.

In this reaction a compound of the formula (V):

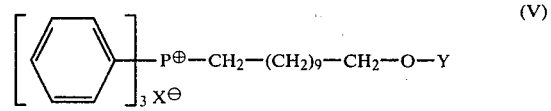

is obtained, wherein Y has the same meaning as defined above and X⊖ stands for a halide ion.

The formula (V) compound is separated from the reaction mixture, treated with metallic potassium, dissolved in hexalkylphosphoric acid triamine, preferably hexamethyl-phosphoric acid triamide, or with dimesyl sodium prepared from dimethyl-sulfoxide with sodium hydride, and then reacted with a compound of formula (IV):

wherein R is as defined above.

The resulting compound of the formula (III):

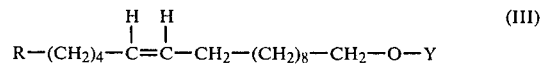

wherein R and Y are defined above, is separated from the reaction mixture.

If this compound contains a Y protecting group other than acetyl, the protecting is split off by hydrolysis, and the resulting compound of the formula (II):

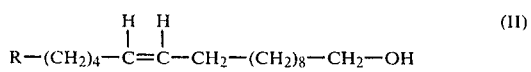

wherein R is as defined above, is treated with an acetylating agent, or the Y protecting group of the formula (III) compound is replaced by an acetyl group. Finally, the resulting compound of the formula (I) is separated from the reaction mixture.

According to a preferred method of the invention one proceeds as follows:

A formula (VII) compound, wherein X stands for halogen, is acetylated. Preferably acetic anhydride is used as acetylating agent. The resulting compound of the formula (VIa):

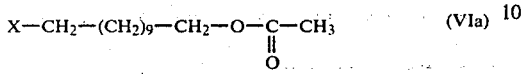

wherein X is as defined above, is reacted with triphenyl phosphine in a solvent medium such as acetonitrile, in the presence of a base such as potassium carbonate.

The resulting compound of the formula (Va):

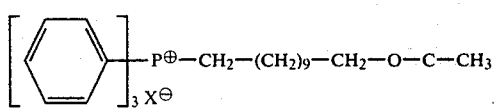

wherein $X^{\ominus}$ is a halide ion, is optionally separated from the reaction mixture, treated with dimesyl sodium prepared by reacting dimethyl sulfoxide with sodium hydride, and then reacted with a compound of the formula (IV), wherein R is as defined above. The resulting compound of the formula (I), wherein R is as defined above, is separated from the reaction mixture.

The compounds of the formulae (I) and (II), wherein R represents a methyl group, are new substances. The compounds of the formulae (III), (V), (Va), (VI) and (VIa) have not been described, as far as we are aware, in the literature either.

Preferred features of the invention include the following:

A compound of the formula:

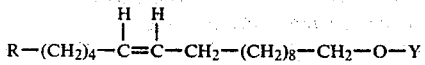

wherein R is methyl and Y is hydrogen, tetrahydropyranyl, 1-ethoxyethyl, or acyl; or R is hydrogen and Y is tetrahydropyranyl, 1-ethoxyethyl or $C_3$ to $C_8$ alkanoyl.

A further preferred feature of the invention includes a compound as defined above wherein R is methyl and Y is hydrogen, tetrahydropyranyl, 1-ethoxyethyl or $C_1$ to $C_6$ alkanoyl.

Another preferred feature of the invention includes a compound of the formula:

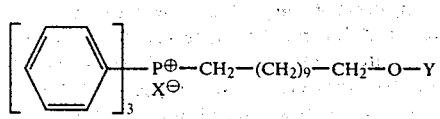

wherein Y is tetrahydropyranyl, 1-ethoxyethyl or acyl.

A further preferred feature of the invention invloves compounds as defined above wherein the acyl group is a $C_1$ to $C_6$ alkanoyl. A most preferred feature includes a compound defined above wherein the acyl is acetyl.

Another preferred feature of the invention includes a compound of the formula:

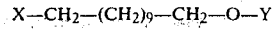

wherein X is halogen and Y is tetrahydropyranyl, 1-ethoxyethyl or $C_1$ to $C_6$ alkanoyl.

A further preferred feature of the invention includes a compound of the formula:

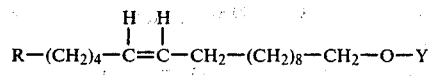

wherein R is methyl and Y is tetrahydropyranyl, 1-ethoxyethyl or acyl; or R is hydrogen and Y is tetrahydropyranyl, 1-ethoxyethyl or $C_3$ to $C_6$ alkanoyl.

A further preferred feature of the invention includes a compound as defined above wherein R is methyl and Y is tetrahydropyranyl, 1-ethoxyethyl or $C_1$ to $C_6$ alkanoyl.

The two-component mixture of active agents according to the invention can be converted into an insect-attracting composition, e.g. by dissolving the two components in inert, less volatile oils, or by enveloping them in capsules or microcapsules.

The insect trap according to the invention contains a combination of the two active agents in a total amount of 0.1 to 10.0 mg, preferably 1 to 3 mg, advantageously in the form of a solution or capsule as discussed above.

In the air-permeation method of the invention for disrupting the mating of the cabbage moth, the combination of the two active agents is preferably emitted into the atmosphere with a speed of 1.0 to 20.0 mg/hectare/hr, more preferably 3.0 to 10.0 mg/hectare/hr.

SPECIFIC EXAMPLES

The moths used in the tests were obtained from a laboratory breed cultivated continuously on a semisynthetic nutrient [cf. B. Nagy: Acta Phytopath. Acad. Sci. Hung. 5, 73–79 (1970)]. The conditions of cultivation were as follows:

temperature: 28° C.;
relative air humidity: about 50 to 60%;
light/dark photoperiods: 18/6.

The nymphs obtained from the culture were sorted according to their sexes and incubated at 25° C. with an inverse photoperiod (dark from 9:00 AM to 3:30 PM and light from 3:30 PM to 9:00 AM).

The NMR spectra were recorded at 60 MHz on a Perkin-Elmer type apparatus.

EXAMPLE A

Examination of the response produced on male cabbage moths in a laboratory biotest 4 male cabbage moths, each 3 to 5 days in age, were put into 200 ml glass vessels and the vessels were covered with glass plates. 4 hours after the beginning of the dark period, a 10×10 mm piece of filter paper, impregnated with 5 μl of n-hexane, was put into the vessels, and the moths were kept under observation for 120 seconds. The number of moths showing motility was registered; this number is regarded as control activity. Thereafter, the above test was repeated with the difference that a piece of filter paper impregnated with 5 μl of an n-hexane solution of the active agent or active agent mixture to be tested [i.e. (Z)-11-hexadecenyl acetate (further on: Z-11-16-ac or component A) and (Z)-11-heptadecenyl acetate (further on: Z-11-17-ac or component B)] was put into the vessels. The behavior of the moths was observed again for 120 seconds. Crawling with wing vibration, groping-about movements and flying were regarded as adequate responses.

The value obtained in the individual control tests were combined into a general average basic activity, and this average value was compared to the average activity values obtained for the individual active agents or active-agent mixtures. The mean values were compared by t-test, and the $ED_{50}$ values were calculated by linear regression.

The results are listed in Tables 1 and 2.

The activities of the 98:2 and 91:9 mixtures of Z-11-16-ad and Z-11-17-ac do not differ significantly from each other on the dosage level of 0.8 ng.

In a dosage of 4 ng. the 98:2, 91:9 and 70:30 mixtures of Z-11-16-ac and Z-11-17-ac provoke far stronger reactions than Z-11-17-ac alone (P=5%). The response produced by the mixtures do not differ, however, significantly from each other.

The situation is the same at the dosage level of 8 ng; the responses produced by the mixtures differ more

TABLE 1

| Dosage ng. | (Z)-11-16-ac (Component A) | Z-11-17-ac (Component B) | Mixtures of components A and B, % by wt. | | | Control activity |
|---|---|---|---|---|---|---|
| | | | 98:2 | 91:9 | 70:30 | |
| 0.4 | — | — | — | $29.0^a$(r=12) | — | $4.1^b$(r=12) |
| 0.8 | — | — | $25.0^a$(r=13) | $30.0^a$(r=15) | $9.37^{ab}$(r=8) | $6.6^b$(r=35) |
| 4.0 | — | $10.4^a$(r=9) | $54.2^b$(r=12) | $50.0^b$(r=15) | $41.6^b$(r=12) | $4.9^a$(r=48) |
| 8.0 | $13.2^a$(r=17) | $11.8^a$(r=14) | $59.0^b$(r=11) | $58.3^b$(r=18) | $53.8^b$(r=13) | $4.1^a$(r=73) |
| 40.0 | $45.8^b$(r=16) | $18.1^a$(r=15) | — | $71.4^c$(r=14) | — | $3.8^a$(r=45) |
| 80.0 | $61.7^a$(r=22) | $48.3^a$(r=15) | — | — | — | $3.7^b$(r=37) |
| 400.0 | — | $51.0^a$(r=9) | — | — | — | $6.9^b$(r=9) | r=number of repetitions
The averages indicated with identical letters (a or b) in the same rows do not differ significantly from each other.

TABLE 2

| Substance | | $ED_{50}$ | | F value of linear fit | Significance level |
|---|---|---|---|---|---|
| Z-11-16-ac | | 47.0 (31.4–70.3) | ng | 1141.30 P | 0.01 |
| Z-11-17-ac | | 334 (27–4214) | ng | 12.62 P | 0.05 |
| Z-11-16-ac 98 | Z-11-17-ac 2 | 3.81 (0.45–32.3) | ng | 35.21 | not significant |
| Z-11-16-ac 91 | Z-11-17-ac 9 | 4.19 (2.81–6.25) | ng | 173.80 P | 0.01 |
| Z-11-16-ac 70 | Z-11-17-ac 30 | 6.40 (4.1–10.0) | ng | 1221.91 P | 0.05 |

The average responses produced on male cabbage moths by the pheromone components or mixtures are listed in Table 1.

When Z-11-17-ac was used alone, a response differing signficantly from the control activity could be attained only with a dosage of 80 ng. At the dosage level of 400 ng the percentage difference increased further; in both instances a significant difference from the control could be observed at the 1% level.

When Z-11-16-ac was used alone, a response differing significantly from the control activity at the 1% level could be attained already with a dosage of 40 ng. With higher dosages the average of the response increased, its maximum value amounted to 61.7%.

When a 91:9 mixture of Z-11-16-ac and Z-11-17-ac was used, a response higher than the control could be attained even with dosages of 0.4 ng and 0.8 ng., a significant difference being only on the 5% level. Upon increasing the dosage the significance improved (1%), and the maximum response was 71.4%.

The situation was similar with the 98:2 mixture of Z-11-16-ac and Z-11-17-ac; in this instance a response diverging from the control on the 5% level was obtained with a dosage of 0.8 ng.

The response produced with the 70:30 mixture diverged from the control only at a dosage of 4 ng.

From the above data it follows that both components possess biological activities characteristic of the natural pheromones, whereas their mixtures exert stronger effects.

When comparing the substances or mixtures tested with respect to the activity strengths, the following observations can be made:

significantly from those produced by Z-11-17-as and Z-11-16ac alone (P=1%). At this dosage level the responses provoked by the two indivdual components (Z-11-17-ac and Z-11-16-ac) do not differ from each other, and only a small difference in activity can be observed between the three mixtures.

In a dosage of 40 ng. the mixtures have the most potent stimulating effects again; their effects differ on the P=5% level from that of Z-11-16-ac and on the P=1% level from that of Z-11-17-ac. The response provoked by Z-11-16-ac increases as well, it differs on the P=5% level from that of Z-11-17-ac with lower activity.

In a dosage of 80 ng. Z-11-16-ac exerts an even more potent stimulating effect on the males but this effect does not differ significantly from that provoked by Z-11-17-ac.

From the above data the following conclusions can be drawn:

When applied alone, Z-11-17-ac exerts the lowest activity, and Z-11-16-ac is more active. However, when admixed with Z-11-16-ac, Z-11-17-ac synergistically increases the activity of the former component. The 98:2 and 91:9 mixtures of Z-11-16-ac and Z-11-17-ac are the most active ones.

This conclusion is also supported by the analysis of the $ED_{50}$ values indicated in Table 2. The $ED_{50}$ values indicated in Table 2. The $ED_{50}$ value represents a dosage which provokes a positive response in 50% of the males treated.

The $ED_{50}$ value of Z-11-17-ac is 334 ng., whereas that of Z-11-16-ac is 47.0, i.e. lower by about one order of magnitude. A further lowering by one order of magnitude occurs with the 98:2 and 91:9 mixtures of Z-11-16-ac and Z-11-17-ac; in these instances the $ED_{50}$ values are 3.89 ng. and 4.19 ng., respectively. These values can be considered as identical, taking into account the wide confidence limit of the $ED_{50}$ value belonging to the 98:2 mixture. The $ED_{50}$ value of the 70:30 mixture is 6.40 ng., i.e. somewhat higher than those of the former two mixtures, but still far lower than that of Z-11-16-ac.

EXAMPLE B

Response of male cabbage moths, kept in an atmosphere containing a 9:1 mixture of Z-11-16-ac and Z-11-17-ac, to the sex pheromone of the females This test aims at elucidating whether the stimulability of males changes or not when kept in an atmosphere containing the major component of the natural sex pheromone mixture. 4 male cabbage moths, each 3 to 5 days of age, were placed into 200 ml glass vessels, and the vessels were covered with glass plates. At the beginning of the dark period, a 10×10 mm piece of filter paper, impregnated with 100 μg of a 9:1 mixture of Z-11-16-ac and Z-11-17-ac dissolved in 5 μl of n-hexane, was placed into the vessels. In the control series filter papers impregnated with 5 μl of n-hexane alone were used. 4 hours after the beginning of the dark period a 10×10 mm piece of filter paper was put again into the vessels; a pheromone gland obtained from a female moth showing attracting behavior was pressed with a glass rod on to the filter papers. The number of males showing motility was registered for 120 seconds. The averages of the responses were compared to each other by the t-test.

The results are listed in Table 3.

TABLE 3

| TREATMENT | STIMULATION | RESPONSE OF MALES, % |
|---|---|---|
| 9:1 mixture of Z-11-16-ac and Z-11-17-ac | one female pheromone gland | 6.25 (r=8) |
| n-Hexane | one female pheromone gland | 71.8 (r=8) | r = number of repetitions.

The averages of the responses by the males differ significantly from each other at the 1% level.

71.8% of the males pre-treated with n-hexane gave a positive response upon stimulation with female pheromone gland, whereas of the males kept in an atmosphere containing a 9"1 mixture of Z-11-16-ac and Z-11-17-ac only 6.25% have a positive response (P=1%). These results indicate that when kept in an atmosphere containing Z-11-16-ac and Z-11-17-ac in a weight ratio of 9:1, the males lose their normal affinity to natural female pheromone. Thus the composition can be applied by the air-permeation technique.

EXAMPLE 1

Preparation of Z-11-heptadecenyl acetate (Formula I, R=CH$_3$)

($a_1$) 11-Bromo-1-undecanol-tetrahydropyranyl ether (Formula VI, X=Br, Y=tetrahydropyranyl)

Three drops of concentrated hydrochloric acid are added to a 0° C. solution of 10 g (0.0398 moles) of 11-bromo-1-undecanol (Formula VII, X=Br) in 5 g (5.4 ml, 0.059 moles) of freshly distilled 3,4-dihydro-2H-pyran, and the mixture is stirred at room temperature for 3 hours. The excess of 3,4-dihydro-2H-pyran is evaporated in vacuo on a 35° C. water bath. The crude 11-bromo-1-undecanol-tetrahydropyranyl ether (Formula VI, X=Br, Y=tetrahydropyranyl) obtained as a residue is sufficiently pure to use it in the next step.

NMR (CDCl$_3$): δ=1.25–2.2 (24H, m), 3.5 (6H, m), 4.5 (1H, m).

($a_2$) 1-(1-Ethoxyethoxy-11-bromo-undecane (Formula VI, X=Br, Y=CHCH$_3$OCH$_2$CH$_3$)

Two drops of concentrated hydrochloric acid are added to a 0° C. mixture of 10 g (0.0398 moles) of 11-bromo-1-undecanol (Formula VII, X=Br) and 3.6 g (0.05 moles) of freshly distilled ethyl-vinyl ether, and the reaction mixture is stirred at room temperature for one hour. The excess of ethyl-vinyl ether is evaporated in vacuo on a 30° C. water bath. The crude 1-(1-ethoxyethoxy)-11-bromo-undecane (Formula VI, X=Br, Y=CHCH$_3$OCH$_2$CH$_3$) obtained as a residue is sufficiently pure to use it in the next step.

NMR (CDCl$_3$): δ=1.3 (24H, m), 3.45 (6H, m), 4.65 (1H, q, J=6 Hz).

($b_1$) Triphenyl-(11-tetrahydropyranyloxy-undecyl)-phosphonium bromide (Formula V, X=Br, Y=tetrahydropyranyl).

A solution of 13.0 g (0.0388 moles) of crude 11-bromo-1-undecanol tetrahydropyranyl ether (Formula VI, X=Br, Y=tetrahydropyranyl), 11 g (0.042 moles) of triphenyl phosphine and 0.5 g of potassium carbonate in 30 ml of dry acetonitrile is refluxed for 10 hours. The solution is cooled, diluted with 200 ml of dry ether, the separated oily substance is isolated by pouring off the ether phase, and this operation is repeated twice with 100 ml each of dry ether. The resulting oily, hygroscopic triphenyl-(11-tetrahydropyranyloxy-undecyl)-phosphonium bromide (Formula V, X=Br, Y=tetrahydropyranyl) is dried in vacuo. 19 g (82%) of the required product are obtained.

NMR (CDCl$_3$): δ=(1.2–2 (24H, m), 3–4 (6H, m), 4.5 (1H, m), 7.5–8.3 (15H, m).

($b_2$) Triphenyl-11-(1-ethoxyethoxy-undecyl)-phosphonium bromide (Formula V, X=Br, Y=CHC-H$_3$OCH$_2$CH$_3$)

A solution of 9.69 g (0.03 moles) of crude 1-(1-ethoxyethoxy)-11-bromo-undecane (Formula VI, X=Br, Y=CHCH$_3$OCH$_2$CH$_3$), 7.86 g (0.03 moles) of triphenyl phosphine and 0.5 g of potassium carbonate in 40 ml of dry acetonitrile is refluxed for 16 hours. The solution is cooled, diluted with 200 ml of dry ether, and the upper ether phase is poured off from the separated oily substance. This operation is repeated twice with 100 ml each of dry ether. The resulting oily, hygroscopic triphenyl-11-(1-ethoxyethoxy-undecyl)-phosphonium bromide (Formula V, X=Br, Y=CHCH$_3$OCH$_2$CH$_3$) is dried in vacuo. 13 g (74%) of the aimed product are obtained.

($c_1$) Tetrahydropyranyl ether of Z-11-heptadecenol (Formula III, R=CH$_3$, Y=tetrahydropyranyl)

(A) 15 ml of dry dimethyl sulfoxide are introduced into a four-necked 100 ml flask equipped with a stirrer, a gas inlet tube, a thermometer and a condenser fitted with a calcium chloride tube. 1.1 g (0.037 moles) of sodium hydride as a 80% oily suspension are added to the liquid, and the reaction mixture is stirred at 70° C. until the gas evolution ceases (about 0.5 hours).

The reaction mixture is cooled to room temperature, a solution of 10.5 g (0.017 moles) of triphenyl-(11-tetrahydropyranyloxy-undecyl)-phosphonium bromide (Formula V, X=Br, Y=tetrahydropyranyl) in 10 ml of dry dimethylsulfoxide is added, and the mixture is stirred at 50° C. for 0.5 hours. The red solution is cooled to room temperature, 1.7 g (2.1 ml, 0.017 moles) of freshly distilled hexanal (Formula V, R=CH₃) are added dropwise and the mixture is stirred for 3 hours.

The mixture is poured onto 30 g of ice and extracted with 150 ml of hexane. The extract is washed successively with water, 10% aqueous sulfuric acid, water, saturated aqueous sodium bicarbonate solution and again with water, dried over magnesium sulfate, filtered, and the solvent is distilled off in vacuo. 4.65 g (82%) of Z-11-heptadecenyl-tetrahydropyranyl ether (Formula III, R=CH₃, Z=tetrahydropyranyl) are obtained as a residue.

Analysis for $C_{22}H_{42}O_2$ (338.55): Calculated: C 78.04%; H 12.51%; Found: C 77.86%; H 12.37%.

IR (NaCl): 1460, 1380, 1370, 1355, 1350, 1140, 1120, 1080, 1035 cm⁻¹.

NMR (CCl₄): $\delta$=0.9 (3H, t, J=7 Hz), 1.1-1.7 (28H, m), 1.9 (4H, m), 3.5 (4H, m), 4.5 (1H, m), 5.25 (2H, t, J=6 Hz).

(B) 1.4 g (0.0358 moles) of metallic potassium are dissolved with stirring in 40 ml of dry hexamethyl-phosphoric acid triamide under argon atmosphere. The dissolution requires about 2 hours. Thereafter a solution of 16.7 g (0.028 moles) of triphenyl-(11-tetrahydropyranyloxy-undecyl)phosphonium bromide (Formula V, X=Br, Y=tetrahydropyranyl) in 50 ml of dry hexamethylphosphoric acid triamide is added dropwise to the mixture.

The reaction mixture is stirred at room temperature for 1.5 hours under reduced pressure (water-jet pump), then cooled to 0° C., and 3 g (3.7 ml, 0.03 moles) of hexanal (Formula V, R=CH₃) are added dropwise.

The resulting mixture is stirred at room temperature for 12 hours. The mixture is poured onto 200 ml of water and extracted with 300 ml of hexane. The hexane solution is washed successively with 5% aqueous sulfuric acid, water, 20% aqueous sodium bisulfite solution and again with water, dried over magnesium sulfate, filtered, and the solvent is evaporated in vacuo. 20 ml of dry hexane are added to the oily residue, the mixture is cooled to 0° C., and the separated triphenyl-phosphine-oxide is filtered off. The filtrate is evaporated to obtained 8 g of Z-11-heptadecenol-tetrahydropyranyl ether (Formula III, R=CH₃, Y=tetrahydropyranyl), identical with the product obtained in step (A).

(c₂) 1-(1-Ethoxyethoxy)-11(Z)-heptadecene (Formula III, R=CH₃, Y=CHCH₃OCH₂CH₃)

1.1 g (0.037 moles) of sodium hydride in an 80% oily suspension are added to 15 ml of dry dimethyl sulfoxide, and the mixture is stirred under argon atmosphere until the gas evolution ceases (about 0.5 hours). The reaction mixture is cooled to room temperature, then a solution of 11.7 g (0.02 moles) of triphenyl-11-(1-ethoxyethoxy)-undecyl-phosphonium bromide (Formula V, X=Br, Y=CHCH₃OCH₂CH₃) in 15 ml of dry dimethylsulfoxide is added, and the resulting mixture is stirred at 50° C. for 0.5 hours.

The solution is cooled to room temperature, then 2.0 g (0.02 moles) of freshly distilled hexanal (Formula IV, R=CH₃) are added dropwise, and the resulting mixture is stirred at room temperature for 8 hours under argon atmosphere.

The mixture is poured onto 30 g of ice and extracted with 150 ml of hexane. The extract is washed with water, 10% aqueous sulfuric acid and again with water, dried over magnesium sulfate, filtered, and the solvent is evaporated in vacuo. 4.4 g (67.5%) of 1-(ethoxyethoxy)-11(Z)-heptadecene (Formula III, R=CH₃, Y=CHCH₃OCH₂CH₃) are obtained as a residue.

NMR (CDCl₃): $\delta$=0.9 (3H, t, J=7 Hz), 1.3 (28H, m), 3.5 (4H, m), 4.65 (1H, q, J=6 Hz), 5.45 (2H, m).

(d₁) (Z)-11-Heptadecenyl acetate (Formula I, R=CH₃)

(A) A mixture of 5.7 g (0.026 moles) of (Z)-11-heptadecenol-tetrahydropyranyl ether (Formula III, R=CH₃, Y=tetrahydropyranyl), 10 ml of acetic acid and 3 ml of acetyl chloride is boiled on an oil bath of about 80° C. for 3 hours. The mixture is cooled, poured onto 30 g. of ice, and extracted with 100 ml. of hexane. The hexane solution is washed with water, dried over magnesium sulfate, the solvent is evaporated, and the residue is distilled in fine vacuo. 2.6 g. (51.6%) of (Z)-11-heptadecenyl acetate (Formula I, R=CH₃) are obtained; b.p.: 122°-126° C./0.05 mmHg.

Analysis for $C_{19}H_{23}O_2$ (296.48): Calculated: C 76.97%; H 12.24%; Found C 76.72%; H 11.98%.

IR (NaCl): 1740, 1460, 1380, 1360, 1230, 1040 cm⁻¹.

NMR (CDCl₃): $\delta$=0.9 (3H, t, J=7 Hz), 1.3 (22H, m), 2 (7H, s+m), 6.05 (2H, t, J=7 Hz), 5.35 (2H, m).

Mass spectrum: m/e 236 (26.9%), 152 (10.4), 138 (13.7), 124 (16.6), 110 (39.4), 96 (75.7), 83 (37.1), 82 (81.4), 81 (56.0), 69 (41.7), 61 (12.1), 55 (68.2), 43 (46.5), 28 (100).

GC: $t_R$=8.25 minutes (SP 2401 10%, Chrom.G. 60-80 mesh, L=4 m, $\phi$=2 mm, T=230° C., $\Delta$p=2.3 att).

(B) 5 g. of (Z)-11-heptadecenol-tetrahydropyranyl-ether (Formula III, R=CH₃, Y=tetrahydropyranyl) are dissolved in 30 ml. of methanol. 4-5 drops of hydrochloric acid are added to the solution, and the mixture is stirred at room temperature for 3 hours. The reaction mixture is poured into water and extracted with 100 ml. of methylene chloride. The extract is washed with water, dried over magnesium sulfate, filtered, and the solvent is evaporated in vacuo. 2.8 g. of (Z)-11-heptadecenol (Formula II, R=CH₃) are obtained as a residue.

Analysis for $C_{17}H_{34}O$ (254.44): Calculated: C 80.24%; H 13.47%; Found: C 79.96%; H 13.21%.

IR (NaCl): 3400, 1460, 1380, 1050 cm⁻¹.

NMR (CCl₄): $\delta$=0.9 (3H, t, J=7 Hz), 1.3 (22H, m), 2 (4H, m), 3.5 (2H, m), 4.5 (1H, m), 5.3 (2H, m).

The obtained (Z)-11-heptadecenol (Formula II, R=CH₃) is added to a mixture of 5 ml. of dry pyridine and 3.5 ml of acetic anhydride, and the mixture is stirred at 0° C. for 3 hours. The solution is poured onto ice and extracted with methylene chloride. The extract is washed with water, 3% aqueous sulfuric acid and again with water, dried over magnesium sulfate, filtered, and the solvent is evaporated. The residue is distilled in fine vacuo. 2.25 g (42%) of (Z)-11-heptadecenyl acetate (Formula I, R=CH₃) are obtained; this compound is identical with the product obtained in step (A) above.

(C) 4 g (0.012 moles) of 1-(1-ethoxyethoxy)-11(Z)-heptadecene (Formula III, R=CH₃, Y=CHCH₃OCH₂CH₃) are added to a mixture of 8 ml. of acetic acid and 2.5 ml. of acetyl chloride, and the mixture is boiled on an oil bath of about 80° C. for 3 hours. The mixture is cooled, poured onto 20 g. of ice and extracted with 100 ml. of hexane. The extract is washed with water, dried over magnesium sulfate, filtered, and the solvent is evaporated. The residue is distilled in fine vacuo. 2.2 g. (62%) of (Z)-11-heptadecenyl acetate are obtained; b.p.: 120°-126° C./0.05 mmHg. This product is identical with the compound obtained in step (A) above.

EXAMPLE 2

Preparation of (Z)-11-hexadecenyl acetate (Formula I, R=H)

(a) Z-11-Hexadecenol-tetrahydropyranyl ether (Formula III, R=H, Y=tetrahydropyranyl)

(A) 1.4 g (0.0358 moles) of potassium are dissolved with stirring, under argon, atmosphere, in 40 ml of dry hexamethyl phosphoric acid triamide. The dissolution requires about 2 hours. A solution of 16.7 g (0.028 moles) of triphenyl-(11-tetrahydropyranyloxyundecyl)-phosphonium bromide (Formula V, X=Br, Y=tetrahydropyranyl) in 50 ml of dry hexamethylphosphoric acid triamide is added dropwise to the mixture, and the resulting mixture is stirred at room temperature for 1.5 hours under reduced pressure (water jet pump).

Thereafter the mixture is cooled to 0° C. 2.9 g (3.6 ml, 0.0336 moles) of pentanal (Formula IV, R=H) are added dropwise, and the resulting mixture is stirred at room temperature for 12 hours.

The reaction mixture is poured into 200 ml of water and extracted with 300 ml of hexane. The hexane solution is washed successively with 5% aqueous sulfuric acid, water, 20% aqueous sodium bisulfite solution, and again with water, dried over magnesium sulfate, and the solvent is evaporated in vacuo. The oily residue is admixed with 20 ml of hexane, the mixture is cooled to 0° C., and the separated triphenylphosphine-oxide is filtered off. The filtrate is evaporated to obtain 7.5 g (82.6%) of (Z)-11-hexadecenol-tetrahydropyranyl ether (Formula III, R=H, Y=tetrahydropyranyl) as a residue.

Analysis for $C_{21}H_{40}O_2$ (324.53): Calculated: C 77.72%; H 12.42%; Found: C 78.10%; H 12.20%.

IR (NaCl): 1460, 1380, 1370, 1350, 1140, 1120, 1080, 1035 cm$^{-1}$.

NMR (CCl$_4$): δ=0.9 (3H, t, J=7 Hz), 1.1−1.7 (26H, m), 1.9 (4H, m), 3.5 (4H, m), 4.5 (1H, m), 5.25 (2H, t, J=6 Hz).

(B) 30 ml of dry dimethyl sulfoxide, freshly distilled from lithium aluminum hydride, are poured into a 200 ml four-necked flask equipped with a stirrer, dropping funnel, a gas inlet tube, a thermometer and a condenser connected to a calcium chloride tube. 2.2 g (0.073 moles) of sodium hydride (80% oily suspension) are introduced into the flask under argon atmosphere, and the mixture is stirred at 70° C. until the gas evolution ceases (0.5 to 1 hours).

The reaction mixture is cooled to room temperature, a solution of 20 g (0.0337 moles) of triphenyl-(11-tetrahydropyranyl-undecyl)-phosphonium bromide (Formula V, X=Br, Y=tetrahydropyranyl) in 25 ml of dry dimethyl sulfoxide are added, and the resulting mixture is stirred at 50° C. for 0.5 hours.

The red solution is cooled to room temperature, 2.9 g. (3.58 ml., 0.0337 moles) of freshly distilled pentanal (Formula IV, R=H) are added dropwise, and the resulting mixture is stirred at room temperature for 3 hours. The mixture is poured onto 50 g. of ice and extracted four times with a total amount of 300 ml. of hexane.

The extracts are combined, washed successively with 20 ml. of water, 20 ml. of 10% aqueous sulfuric acid, 20 ml. of water, 20 ml. of saturated aqueous sodium bicarbonate solution and again with 20 ml. of water, dried over magnesium sulfate, filtered, and the solvent is evaporated in vacuo. 9 g. (82.5%) of (Z)-11-hexadecenol-tetrahydropyranyl ether (Formula III, R=H, Y=tetrahydropyranyl) are obtained; this compound is identical with the substance prepared according to step A) above.

(b) (Z)-11-Hexadecenyl acetate (Formula I, R=H)

(A) 9 g. of (Z)-11-hexadecenol-tetrahydropyranyl ether (Formula III, R=H, Y=tetrahydropyranyl) are dissolved in 25 ml. of acetic acid. 6 ml. of acetyl chloride are added, and the solution is boiled on an oil bath of about 80° C. for 3 hours. The mixture is cooled, poured onto 50 g. of ice, and extracted thrice with a total amount of 200 ml. of hexane. The extracts are combined, washed with 30 ml. of water, dried over magnesium sulfate, filtered, and the solvent is evaporated. The residue is distilled off in fine vacuo. 5.3 g. (55.7%) of (Z)-11-hexadecenyl acetate are obtained; b.p.: 142°−144° C./0.25 mmHG.; 120°−122° C./0.05 mmHg.

Analysis for $C_{28}H_{34}O_2$ (282.45): Calculated: C 76.54%; H 12.13%; Found: C 76.42%; H 12.00%.

IR (NaCl): 1740, 1650, 1460, 1380, 1365, 1235, 1040 cm$^{-1}$.

NMR (CDCl$_3$): δ=0.9 (3H, t, J=7 Hz), 1.3 (20H, m), 2 (7H, s+m), 6.05 (2H, t, J=7 Hz), 5.35 (2H, m).

Mass spectrum: m/e 223 (31%), 138 (14.9), 124 (20.8), 110 (43.3), 97 (95.5), 83 (100), 82 (74.8), 70 (56.7), 69 (88.7), 57 (13.4), 55 (98.9), 44 (69.2).

GC: $t_R$=8.05 minutes (SP 2401 10%, Chrom. G. 60−80 mesh, L=4 m, φ2 mm, t=230° C., Δp=2.3 att).

(B) 5 g. of (Z)-11-hexadecenol-tetrahydropyranyl ether (Formula III, R=H, Y=tetrahydropyranyl) are dissolved in 30 ml. of methanol, and 3 to 4 drops of hydrochloric acid are added. The solution is stirred at room temperature for 3 hours. The reaction mixture is poured into water and extracted with 100 ml. of methylene chloride. The extract is washed with water, dried over magnesium sulfate, filtered, and the solvent is evaporated in vacuo. 3 g. of Z-11-hexadecenol (Formula II, R=H) are obtained as a residue.

Analysis for $C_{16}H_{32}O$ (240.42): Calculated: C 79.92%; H 13.42%; Found: C 79.64%; H 13.25%.

IR (NaCl): 3400, 1460, 1380, 1050 cm$^{-1}$.

NMR (CCl$_4$): δ=0.9 (3H, t, J=7 Hz), 1.5 (20H, m), 2 (4H, m), 3.5 (2H, m), 4.5 (1H, m), 5.3 (2H, m).

The obtained (Z)-11-hexadecenol (Formula II, R=H) is added to a mixture of 5 ml. of dry pyridine and 4 ml. of acetic anhydride, and the mixture is stirred at 0° C. for 3 hours. The solution is poured onto ice and extracted with methylene chloride. The extract is washed with water, 3% aqueous sulfuric acid and again with water, dried over magnesium sulfate, filtered, and the solvent is evaporated. The residue is distilled in fine vacuo. 2.2 g (40%) of (Z)-11-hexadecenyl acetate (Formula I, R=H) are obtained; the product is identical with the substance obtained according to step (A) above.

EXAMPLE 3

Preparation of (Z)-11-heptadecyl acetate (Formula I, R=CH$_3$)

(a) 11-Bromo-undecanol acetate (Formula III, X=Br, Y=COCH$_3$)

A solution of 30 g. (0.12 moles) of 11-bromo-1-undecanol (Formula III, X=Br) and 15 ml. (0.15 moles) of acetic anhydride in 100 ml. of dry benzene is allowed to stand at room temperature for one day. The solvent is evaporated, and the residue is distilled in vacuo. 31.4 g. (89.7%) of 11-bromoundecanol acetate (Formula VI, X=Br, Y=COCH$_3$) are obtained; b.p.: 120° C./0.1 mmHg.

Analysis for C$_{13}$H$_{25}$O$_2$Br (293.2): Calculated: C 53.28%; H 8.59%; Br 27.27%; Found: C 53.42%; H 8.69%; Br 26.90%.

IR (NaCl): 1735, 1460, 1440, 1390, 1360, 1230, 1040 cm$^{-1}$.

NMR (CDCl$_3$): δ=1.3 (18H, m), 1.96 (3H, s), 3.35 (2H, t, J=7 Hz), 3.95 (3H, t, J=7 Hz).

(b) Triphenyl-(11-acetoxy-undecyl)-phosphonium bromide (Formula V, X=Br, Y=COCH$_3$)

A solution of 30 g. (0.102 moles) of 11-bromo-undecanol acetate (Formula VI, X=Br, Y=COCH$_3$), 26.72 g. (0.102 moles) of triphenyl phosphine and 0.5 g. of potassium carbonate in 100 ml. of dry acetonitrile is refluxed for 15 hours. The solution is cooled, diluted with 200 ml. of dry ether, and the upper ether phase is decanted from the separated oily substance. This operation is repeated twice with 200 ml. of dry ether. The obtained 45.3 g. (80%) of triphenyl-(11-acetoxy-undecyl)-phosphonium bromide (Formula V, X=Br, Y=COCH$_3$) is dried in vacuo.

IR (NaCl): 1740, 1585, 1490, 1470, 1440, 1390, 1360, 1240, 1150, 1040, 1000 cm$^{-1}$.

NMR (CDCl$_3$): δ=1.2 (14H, m), 1.5 (4H, m), 2 (3H, s), 3.5 (2H, m), 4 (3H, t, J=7 Hz), 7.7 (15H, m).

(c) (Z)-11-Heptadecenyl acetate (Formula I, R=CH$_3$)

30 ml. of dry dimethyl sulfoxide are poured into a 200 ml. of four-necked flask equipped with a stirrer, a dropping funnel, a gas inlet tube, a thermometer and a condenser. 2.5 g. (0.13 moles) of sodium hydroxide (80% oily suspension) are introduced into the flask, and the mixture is stirred at 70° C. under argon temperature until the gas evolution ceases (0.5 hours). The reaction mixture is cooled to room temperature, a solution of 20 g. (0.036 moles) of triphenyl-(11-acetoxy-undecyl)-phosphonium bromide (Formula V, X=Br, Y=COCH$_3$) in 20 ml. of dry dimethyl sulfoxide is added, and the resulting mixture is stirred at room temperature for 0.5 hours. There are added dropwise to the red solution 4 g. (0.04 moles) of hexanel (Formula IV, R=CH$_3$), and the mixture is stirred at room temperature for 15 hours. The reaction mixture is poured onto 60 g. of ice, and extracted with 200 ml. of hexane. The extract is washed successively with water, 10% aqueous sulfuric acid, water, saturated aqueous sodium bicarbonate solution and again with water, dried over magnesium sulfate, filtered, and the solvent is evaporated in vacuo. 2.34 g. (22%) of (Z)-11-heptadecenyl acetate (Formula I, R=CH$_3$) are obtained; b.p.: 122°–125° C./0.05 mmHg.

The obtained product is identical with the substance prepared according to Example 1.

We claim:

1. A composite insect attractant for male cabbage moths (*Mamestra brassicae*), which comprises
   (a) (Z)-11-hexadecyl acetate as a first active agent A and
   (b) (Z)-11-heptadecyl acetate as a second active agent B in a weight ratio of 70 to 99 parts A: 30 to 1 parts B.

2. A composite as claimed in claim 1, which comprises components A and B in a weight ratio of 85 to 95 parts: 15 to 5 parts along with a liquid or solid adjuvant.

3. A composite as claimed in claim 1, further comprising an inert oily diluent as said adjuvant.

4. A process for attracting and trapping male cabbage moths (*Mamestra brassicae*), which comprises exposing said males to the effect of an insect trap containing a combination of (Z)-11-hexadecyl acetate as Component A and (Z)-11-heptadecenyl acetate as Component B in a total amount of 0.01 to 10.0 mg., the combination containing the two components in a weight ratio of 70 to 99 parts A: 30 to 1 parts B.

5. A process for the disruption of the mating of cabbage moths (*Manestra brassicae*), which comprises the step of emitting into the atmosphere at a speed of 1.0 to 20.0 mg/hectare/hr an effective amount of a combination of (Z)-11-hexadecenyl acetate as a Component A and (Z)-11-heptadecenyl acetate as a Component B, wherein the combination contains the two components in a weight ratio of 70 to 99 parts A: 30 to 1 part B.

* * * * *